United States Patent
Kaplan

[11] Patent Number: 5,981,434
[45] Date of Patent: Nov. 9, 1999

[54] HERBICIDAL COMPOSITION FOR THE CONTROL OF EPIPHYTIC WEEDS

[76] Inventor: Jeff Kaplan, P.O. Box 11106, Ft. Lauderdale, Fla. 33339

[21] Appl. No.: 09/090,503

[22] Filed: Jun. 4, 1998

[51] Int. Cl.[6] .................................................. A01N 59/16
[52] U.S. Cl. ............................................................ 504/121
[58] Field of Search ..................................... 504/130, 121

[56] References Cited

U.S. PATENT DOCUMENTS

| | | | |
|---|---|---|---|
| 5,420,098 | 5/1995 | Ansai et al. | 504/133 |
| 5,668,089 | 9/1997 | Shribbs et al. | 504/348 |
| 5,696,024 | 12/1997 | Szamosi | 504/139 |
| 5,719,310 | 2/1998 | Fisher et al. | 560/83 |
| 5,739,326 | 4/1998 | Selby et al. | 544/66 |

OTHER PUBLICATIONS

Royal Society of Chemistry, The Argochemicals Handbook, 3rd ed., 1991.

*Primary Examiner*—S. Mark Clardy
*Assistant Examiner*—Alton Pryor
*Attorney, Agent, or Firm*—Jeffrey Kaplan

[57] ABSTRACT

A herbicidal composition to selectively control undesirable epiphytic weeds by applying active ingredients in an effective amount of Atrazine, Simazine, Dichlobenil, Atrazine+Dichlobenil, Simazine+Dichlobenil and the surfactant Tween 80.

7 Claims, No Drawings

HERBICIDAL COMPOSITION FOR THE CONTROL OF EPIPHYTIC WEEDS

BACKGROUND—FIELD OF INVENTION

This invention relates to novel compositions comprising mixtures of three herbicides and to a method of controlling undesired epiphytic species by the application of an effective amount of one of the herbicides that comprise the mixture, alone or the composition comprising the mixtures.

BACKGROUND—DISCUSSION OF PRIOR ART

The genus Tillandsia which belongs to the Bromeliaceae includes almost 400 species distributed from the south of the United States Of America to the northern part of Patagonia in Argentina. The population of these epiphytic species such as *Tillandsia Recurvata* (Ball Moss) and *Tillandsia Aeranthos* on trees and shrubs in the southernmost areas of the United States has increased dramatically, causing severe deleterious effects on their hosts.

Epiphytes are generically known as symbionic air plants and for two decades have been considered harmless to their hosts. Typically, epiphytic plants are not rooted in soil. Instead, they live above ground level on the stems and branches of other plants and trees. Epiphytes obtain water from trapped rainwater and from moisture in the air. They obtain minerals from organic matter that has accumulated on the surface of the host plant on which they are growing.

The present inventor has studied this extensive growth and the deleterious effects of these epiphytes and has concluded that they should be redefined as epiphytic weeds. These epiphytic weeds have a great multiplication capacity owing to the numerous plume seeds that allow them to fix onto the wrinkled surfaces of trees and branches.

A severe invasion of the growth of these epiphytic weeds cause significant shade that causes light competition and release some kind of growth inhibitor which is responsible for leaf abscission. Resulting from their position on the hosts, epiphytes such as the Tillandsia specie individuals cannot be controlled by cutting or pulling, thus selective herbicides are needed and are in great demand.

The use of selective herbicides to control various weeds is well established in the art. Typical herbicides that are commercially available are 2,4-dichlorophenoxyacetic acid (2,4-D), Copper sulfate. Cutrine, Thiocarbamates. Butylate, CDEC, Diallate, EPTC and many others. The majority of commercially available herbicides that control weeds are limited to soil application where they are readily adsorbed from the soil by roots and translocated via the xylem to the foliage where they inhibit oxygen evolution in photosynthesis.

Typical new herbicidal formulations are set forth in the U.S. Pat. No. 5,420,098 to Hodogaya Chemical Co. Ltd (1995), in U.S. Pat. No. 5,668,089 to Zeneca Ltd (1997), and in U.S. Pat. No. 5,696,024 to American Cyanamid Co. (1997). Unfortunately, these Patent formulations as well as others have many disadvantages such as high toxicity, flammability, and are primarily used in the soil. It has been discovered by the inventor that there is no cited prior art relating to the control of epiphytes. Thus, a need exists for a fast acting herbicide formulation that is specifically designed to control the unique problems associated with epiphytic weeds and their respective physiology.

OBJECTS AND ADVANTAGES

Accordingly, several objects and advantages of my invention are:

(a) to provide a novel herbicidal formulation designed specifically to control the growth of epiphytic weeds.

(b) to provide a novel herbicidal formulation that will be absorbed through the trichomes of the epiphyte.

(c) to provide a novel herbicidal formulation that can be absorbed by the epiphyte without affecting the host species and causing phytotoxic effects on the terminal buds and leaves of the host plant.

(d) to provide a novel herbicidal formulation that is safe for humans and wildlife when used at the recommended doses.

(e) to provide a novel herbicidal formulation that is easily dispersed onto the epiphytes and is inexpensive.

DETAILED DESCRIPTION OF THE INVENTION

In the present invention, the foregoing difficulties are obviated in that there is provided a low cost, easily dispersed formulation consisting of commercially available herbicides. In accordance with the invention, the formulation is initially comprised of three herbicides, Dichlobenil-(2,6-dichlorobensonitrile), Atrazine-(2-chloro-4(ethylamino)-6-(isopropylamino)-s-triazine, and Simazine-(2-chloro-4,6-bis (ethylamino)-s-triazine.

These herbicides can be applied in five different formulations. (1) Dichlobenil 50 wettable powder (WP), 5 $gl^{-1}$+Tween 80 (0.5%), (2) Simazine 80 Wettable Powder (WP), 5 $gl^{-1}$+Tween 80 (0.5%), (3) Atrazine 80 emulsifiable concentrate (EC), 10 $gl^{-1}$+Tween 80 (0.5%), (4) Simazine+Dichlobenil+Tween 80 and (5) Atrazine +Dichlobenil+Tween 80 in the same doses of the formulated product. The Tween 80 is used as a surfactant and is also a wetting agent. The formulation is sprayed onto the foliage of the host and to the epiphytic weeds. The doses are chosen by a dose response assay and is familiar to those skilled in the art. The formulated mixtures can be dispersed using conventional methods such as knapsack, power and bottle sprayers as well as aircraft sprayers. These mixtures produce a synergistic action and have an increase in the effectiveness of the treatment.

During October 1997 to May 1998 in the area of Plantation, Fla., the inventor tested these herbicide formulations on ten different host species which were actively growing and were infested with epiphytes of the Tillandsia species. The following treatments were applied: Atrazine 10 $gl^{-1}$, Dichlobenil 5 $gl^{-1}$, Simazine 5 $gl^{-1}$, Simazine 5 $gl^{-1}$+Dichlobenil 5 $gl^{-1}$ and Atrazine 10 $gl^{-1}$+Dichlobenil 5 $gl^{-1}$. Tween 80 (0.5%) was added to all the formulations.

All the selected herbicides, alone or in combination controlled the epiphytes without causing phytotoxicity to their host plant, owing to the different absorption systems of the epiphytes and their hosts.

The following example is given as specific illustration of the invention. It should be understood, however, that the invention is not limited to the specific details set forth therein.

TABLE 1

Population level of epiphytic species *Tillandsia recurvata* (Number of individuals) before and after treatments: (Tween 80 was included in the formulations)

| Treatment | Oct. 20 | Nov. 20 | Dec. 20 | Feb. 20 | Mar. 20 | April 20 | May 20 |
|---|---|---|---|---|---|---|---|
| | | | | TREATMENT | | | |
| Control | 140 | 135 | 133 | | 156 | 150 | 150 |
| Atrz. & Dich. | 140 | 138 | 139 | | 1 | 1 | 1 |
| Simaz. & Dich. | 140 | 136 | 146 | | 18 | 18 | 18 |
| Atrazine | 140 | 139 | 122 | | 115 | 45 | 3 |
| Simazine | 140 | 140 | 143 | | 22 | 2 | 4 |
| Dichlobenil | 140 | 124 | 117 | | 5 | 1 | 1 |

CONCLUSION, RAMIFICATION AND SCOPE OF THE INVENTION

Accordingly, the reader will see that a selectivly formulated herbicidal composition of the invention provides that:

it will specifically control the growth of epiphytic weed.

it will be absorbed through the trichomes of the epiphytes.

it will be absorbed by the epiphyte without affecting the host species and causing phytotoxic effects on the terminal buds and leaves of the host plant.

it will be safe for humans and wildlife when used at the recommended doses.

it will be inexpensive and easily dispersed using conventional methods.

Those skilled in the art will have no difficulty in determining suitable proportions of the above compositions to be used. The invention has been described as applied to preferred embodiments and it will be understood that various substitutions and changes may be effected without departing from the spirit and scope of the novel concepts and principals of this invention.

I claim:

1. A herbicidal composition consisting essentially of a herbicide or a combination of herbicides selected from a group consisting of Dichlobenil 50 wettable powder, Simazine 80 wettable powder, Atrazine 80 emulsifiable concentrate, Atrazine 80 emulsifiable concentrate and Dichlobenil, Simazine 80 wettable powder and Dichlobenil, plus a surfactant and copper hydroxide.

2. A composition as in claim 1 consisting essentially of 5 g/l of Dichlobenil 50 wettable powder, 0.5% surfactant and copper hydroxide.

3. A composition as in claim 1 consisting essentially of 5 g/l of Simazine 80 wettable powder, 0.5% surfactant and copper hydroxide.

4. A composition as in claim 1 consisting essentially of 10 g/l of Atrazine 80 emulsifable concentrate, 0.5% surfactant and copper hydroxide.

5. A composition as in claim 1 consisting essentially of 5 g/l of Simazine 80 wettable powder, 5 g/l or Dichlobenil 50 wettable powder, 0.5% surfactant and copper hydroxide.

6. A composition as in claim 1 consisting essentially of 10 g/l of Atrazine 80 emulsifable concentrate, 5 g/l of Dichlobenil 50 wettable powder, 0.5% surfactant and copper hydroxide.

7. A method or controlling and eradicating the species tillandsia recurvata and epiphytic weeds which comprises applying the composition of any one of claims 1–6, to the branches and canopies of the infected hosts.

* * * * *